(12) United States Patent
Van Wesenbeeck et al.

(10) Patent No.: US 6,279,380 B1
(45) Date of Patent: Aug. 28, 2001

(54) NONCOMBUSTIVE METHOD OF DETERMINING THE CALORIFIC VALUE OF FUEL GAS

(75) Inventors: Petrus J. M. M. Van Wesenbeeck, Groningen (NL); Manfred Jaeschke, Dorsten (DE); Johannes A. Schouten, Monnickendam (NL); Peter Schley, Dorsten (DE)

(73) Assignees: N. V. Nederlandese Gasunie (NL); Ruhrgas Aktiengesellschaft (DE)

( * ) Notice: Subject to any disclaimer, the term of this patent is extended or adjusted under 35 U.S.C. 154(b) by 0 days.

(21) Appl. No.: 09/315,237

(22) Filed: May 20, 1999

(30) Foreign Application Priority Data

May 20, 1998 (EP) .................................. 98201675
Sep. 29, 1998 (EP) .................................. 98203278

(51) Int. Cl.$^7$ .......................... G01N 33/22; G01N 29/18; G01N 9/00; G01F 15/04
(52) U.S. Cl. .......................... 73/25.01; 73/23.31; 73/597
(58) Field of Search ............... 73/25.01, 23.31, 73/23.2, 592, 597

(56) References Cited

U.S. PATENT DOCUMENTS

| | | | | |
|---|---|---|---|---|
| 2,197,370 | * | 4/1940 | Sullivan | 73/190 |
| 3,264,862 | * | 8/1966 | Felton et al. | 73/25 |
| 3,507,146 | * | 4/1970 | Webb | 73/23 |
| 4,236,406 | * | 12/1980 | Reed et al. | 73/61.1 R |
| 4,255,964 | * | 3/1981 | Morison | 73/24 |
| 5,117,676 | * | 6/1992 | Chang | 73/40.5 A |
| 5,141,331 | * | 8/1992 | Oehler et al. | 374/118 |
| 5,285,675 | * | 2/1994 | Colgate et al. | 73/23.2 |
| 5,360,266 | * | 11/1994 | Lenfers et al. | 374/36 |
| 5,467,637 | * | 11/1995 | Hasegawa et al. | 73/24.01 |
| 5,501,098 | * | 3/1996 | Cadet et al. | 73/24.01 |
| 5,524,477 | * | 6/1996 | Wajid | 73/24.05 |
| 5,537,854 | * | 7/1996 | Phillips et al. | 73/24.01 |
| 5,635,626 | * | 6/1997 | Hammond et al. | 73/23.2 |
| 5,748,492 | * | 5/1998 | Van der Heyden et al. | 364/499 |
| 5,768,937 | * | 6/1998 | Wajid et al. | 73/24.06 |
| 5,886,262 | * | 3/1999 | Sinha | 73/579 |
| 5,948,967 | * | 9/1999 | Cadet et al. | 73/24.01 |

FOREIGN PATENT DOCUMENTS

| | | | |
|---|---|---|---|
| 19808533 | * | 2/1998 | (DE) . |
| 0657736 | * | 12/1994 | (EP) . |
| 0939317 | * | 2/1999 | (EP) . |
| 2333371 | * | 1/1999 | (GB) . |

\* cited by examiner

*Primary Examiner*—Hezron Williams
*Assistant Examiner*—David J. Wiggins
(74) *Attorney, Agent, or Firm*—Pillsbury Winthrop LLP

(57) ABSTRACT

Noncombustive method of measuring the calorific value of fuel gas, wherein a) the speed of sound in the gas is determined under first and under second reference conditions and one of the parameters dielectric constant, speed of sound under third reference conditions or proportion of carbon dioxide in the fuel gas is measured and b) the calorific value is derived from these three parameters, wherein the steps a) and b) are preferably preceded by a plurality of measurement cycles in which step a) is carried out using a plurality of reference gases of known calorific value, a number corresponding to the number of measurement cycles of reference signal patterns determined from the ratio of the various measurement signals measured on the reference gases are stored with assignment to the known calorific values and the signal pattern from a future measurement cycle on fuel gas of unknown calorific value is compared with the reference signal patterns so as to assign a particular calorific value.

19 Claims, 7 Drawing Sheets

NONCOMBUSTIVE METHOD OF DETERMINING THE CALORIFIC VALUE OF FUEL GAS

The invention relates to a noncombustive method of measuring the calorific value of fuel gas and to a use of the method for the noncombustive measurement and/or regulation of the amount of heat supplied to gas consumption devices, in particular to devices for consumption of natural gas. The noncombustive methods of measuring the calorific value or measuring the amount of heat have, compared with calorimetric methods in which controlled combustion of a substream of the gas stream being transferred is carried out, the advantage that they are significantly cheaper. However, practical implementation is frequently complicated, even without taking account of the difficulties which can occur in calibration.

Noncombustive methods of measurement include indirect and correlative methods. In the indirect methods, the gas composition is analysed. The composition of the gas together with the calorific values for the pure substances can then be used to determine the calorific value of the fuel gas. These methods (e.g. gas chromatography) give very accurate results, but are technically complicated and are therefore not very suitable for use in, for example, domestic premises. In addition, they are susceptible to faults. In the correlative methods of measuring the calorific value or the amount of heat, a relationship between a readily measurable physical or chemical parameter and the calorific value is exploited. This makes them technically easier to carry out, but the reproducibility and the accuracy of the measurement of the calorific value or of the amount of heat are restricted to an undesirable degree.

It is an object of the invention to further reduce the outlay in the correlative noncombustive measurement of the calorific value or the measurement and/or regulation of the amount of heat supplied to consuming devices and, in particular, to provide a reliable and accurate measurement method. This object is achieved according to the invention by, in the method mentioned at the outset, a) determining the speed of sound in the gas under first and under second reference conditions and measuring one of the parameters-dielectric constant, speed of sound under third reference conditions or proportion of carbon dioxide in the fuel gas and b) deriving the calorific value from these three parameters.

Particularly accurate results can be achieved for fuel gases whose calorific value at STP is from 20 to 48 Mj/m3, whose relative density compared with dry air is from 0.55 to 0.9, whose proportion of carbon dioxide is less than or equal to 0.3 and whose proportion of hydrogen and carbon monoxide is less than 0.1 and 0.03 respectively. Particularly suitable measurement conditions are temperatures in the range from 225 to 350 K and pressures of less than or equal to 60 MPa.

The first reference conditions set are preferably STP (273.15 K and 1 bar) or a pressure of from 1 to 10 bar, more preferably from 3 to 7 bar. Although the temperature is not very critical and can be selected within a wide range, for technical reasons the temperature is above 225 K, for example from 270 K to 295 K. For the second reference conditions, a pressure of above 30 bar is preferably set. Although the temperature is not very critical and can be selected within a wide range, for technical reasons the temperature is from 225 K to 350 K. Greatest preference is given to the operating conditions for this parameter. The preferred values for the third reference conditions are a pressure of over 150 bar, more preferably over 175 bar, for example 200 bar. When using a third reference condition, the pressure of the second reference condition should preferably be set below 70 bar.

The speed of sound at the reference conditions mentioned, including operating conditions, can be determined in a separate measuring unit, for example via the resonant frequency of pipes or of hollow bodies or a distance travelled-time measurement, e.g. in ultrasound meters. The dielectric constant can be measured inexpensively and with high accuracy even under operating conditions. The proportion of carbon dioxide is simple to determine under all conditions mentioned using known measuring instruments, e.g. by measurement of the light absorption in the infrared region.

Consequently, the three measurements required in each case can be carried out without great technical outlay, reliably and accurately so that the combination of the measured values gives corresponding results for the calorific value. The calorific value determined in this way can be used, for example, for controlling combustion processes.

Depending on the application, it is possible to determine the calorific value on a volume basis under reference or operating conditions, the specific calorific value (on a mass basis) or the molar calorific value. There are a total of three variations of the method of the invention for measuring the calorific value of fuel gas.

In all three variants, the speed of sound is determined under first and under second reference conditions.

In the first variant, the speed of sound is additionally measured under third reference conditions. The determination of two and, in this first variant, even three speeds of sound has the advantage that all measurements can be carried out in one measuring apparatus. The pressure in the apparatus can be varied by compressing the measurement volume or allowing it to expand. On compression or expansion, the temperature of the fuel gas also changes, which can make the setting of altered reference conditions easier. If desired, the measuring apparatus for determining the speeds of sound can be provided with additional means of setting an altered temperature.

In the second variant, not only are the two speeds of sound measured but the dielectric constant is also measured, preferably at a pressure of at least 10 bar to achieve high accuracy, e.g. under second reference conditions, e.g. operating conditions.

In the third variant, the proportion of carbon dioxide in the fuel gas is determined in addition to the two speeds of sound.

The determination of the dielectric constant and the proportion of carbon dioxide can be carried out in the same measuring environment as that in which the speeds of sound are determined. This makes a very compact measuring apparatus possible.

Advantageously, the speed of sound is measured under second reference conditions and the dielectric constant or the proportion of carbon dioxide are measured under the same reference conditions, preferably under operating conditions, in a joint measuring environment. This makes only one temperature and pressure measurement and consequently only one thermostat necessary for setting and maintaining the reference conditions. In addition, uniform reference conditions for the different measurements increase the accuracy to which the amount of heat supplied can be determined.

The determination of at least two speeds of sound offers the further advantage that it is not necessary to determine the density of the fuel gas. Density measurements are, particularly under operating conditions, expensive and complicated. In the method according to the invention, preference is given to not carrying out any additional density measurement, particularly when the proportion of carbon dioxide is determined as a third parameter.

To establish the reference conditions, the parameters temperature and pressure are required. These can be additionally measured in step a). If a lower measurement accuracy is permissible, the values estimates from practice can also be used for these parameters. The measurement accuracy can be further increased by additionally determining the proportion of nitrogen in step a).

To find a suitable correlation between the measured parameters and the calorific value, it is advantageous to precede the respective steps a) and b) at least once by a plurality of measurement cycles in which step a) is carried out using a plurality of reference gases of known calorific value. The parameters required for the various variants of the method are then measured on the reference gas. In these reference cycles, a number corresponding to the number of measurement cycles of reference signal patterns determined from the ratio of the various signals measured are stored with assignment to the known calorific values. The signal pattern from a future measurement cycle on fuel gas of unknown calorific value is compared with the reference signal patterns so as to assign a particular calorific value.

To increase the reference accuracy, many reference cycles in which the various parameters are varied in succession over the expected measurement range should be carried out. An unambiguous and accurate assignment of a particular calorific value to a signal pattern of a fuel gas determined in a measurement cycle is achieved by interpolation of the various reference signal patterns.

A significant advantage is that the correlation between calorific value and measured parameters only has to be found once for a specific application by means of any desired number of reference cycles. The one-off outlay is comparatively low. The reference conditions should here be selected so as to correspond as closely as possible to the measurement conditions expected later. Thus, for all parameters only the measurement ranges which actually come into question should be determined with sufficient accuracy as reference signal patterns.

If the composition of the fuel gas may display greater variations, it is generally necessary to determine more reference signal patterns. An additional advantage of the choice of speeds of sound as the parameters to be determined in the method of the invention is that a great amount of data in respect of the dependence of the gas composition on the speed of sound is already available and that, furthermore, these data can readily be determined experimentally. Use of these data which are already available thus makes it possible to calculate the calorific value and speeds of sound as a function of the gas composition in the relevant range. These data can thus be used for calculating the calorific value from the measured parameters.

A preferred embodiment of the invention is characterized in that, for the purposes of the calculation of the calorific value, the respective proportion of a specified number of alkanes, including methane, is determined by determining the proportion of the individual alkanes, excluding methane, with the aid in each case of an associated function dependent on a selected physical property, preferably the molar calorific value, of the sum of the specified alkanes and in that the proportion of methane is determined from the difference between the proportion of the sum of the specified alkanes and the sum of the proportions of the alkanes determined by means of the functions.

As specified alkanes, all alkanes which are actually present in the fuel gas should, if possible, be selected and specified.

It has been found that the proportions of the alkanes in natural fuel gases are always in a particular ratio to one another which depends only on a physical property, e.g. the molar calorific value, of the sum of the specified alkanes. This is obviously attributable to the fact that natural gases in the form in which they occur have always gone through an equilibrium phase in which their gaseous or liquid phases have been in equilibrium with one another. However, the method is not restricted to natural fuel gases, either with or without addition of coal gas. For synthetic gases containing added substances or for gas mixtures having many components, the uncertainty in the determination of the gas composition is merely somewhat greater.

The molar calorific value of the sum of the specified alkanes can in turn be determined, for example, with the aid of reference signal cycles. Since the composition of the reference gases is known, their molar calorific value of the sum of the specified alkanes is also known. Consequently, from the ratio of the signals measured on the reference gases, a number corresponding to the number of reference measurement cycles of reference signal patterns can be stored with assignment to the known molar calorific values of the sum of the specified alkanes. In a future measurement cycle, the molar calorific value of the sum of the specified alkanes in the fuel gas can be determined merely by comparison of the signals measured with the stored reference signal patterns.

As functions for determining the proportions of the individual alkanes with the exception of methane, use can advantageously be made of polynomials, preferably of second order.

In a preferred illustrative embodiment, the proportions of methane, ethane, propane, isobutane, n-butane, isopentane, n-pentane, hexane, heptane and octane are determined with the aid of the functions. It has been found that the proportion of all further hydrocarbons can be ignored, particularly in the case of natural fuel gas. The relationship between the molar calorific value and the sum of the specified alkanes is in this case, e.g.:

$$X_{C2H6} = [\alpha_2 (H_{CH} - H_{CH4}) + \beta_1 (H_{CH} - H_{CH4})^2] X_{CH} \quad (1.1)$$

$$X_{C3H3} [\alpha_2 (H_{CH} - H_{CH4}) + \beta_2 (H_{CH} - H_{CH4})^2] X_{CH} \quad (1.2)$$

$$X_{i-C4H10} = [\alpha_3 (H_{CH} - H_{CH4}) + \beta_3 (H_{CH} - H_{CH4})^2] X_{CH} \quad (1.3)$$

$$X_{n-C4H10} = [\alpha_4 (H_{CH} - H_{CH4}) + \beta_4 (H_{CH} - H_{CH4})^2] X_{CH} \quad (1.4)$$

$$X_{i-C5H12} = [\alpha_5 (H_{CH} H_{CH4}) + \beta_5 (H_{CH} - H_{CH4})^2] X_{CH} \quad (1.5)$$

$$X_{n-C5H13} = [\alpha_6 (H_{CH} - H_{CH4}) + \beta_6 (H_{CH} - H_{CH4})^2] X_{CH} \quad (1.6)$$

$$X_{n-C6H14} = [\alpha_7 (H_{CH} - H_{CH4}) + \beta_7 (H_{CH} - H_{CH4})^2] X_{CH} \quad (1.7)$$

$$X_{n-C7H16} = [\alpha_8 (H_{CH} - H_{CH4}) + \beta_8 (H_{CH} - H_{CH4})^2] X_{CH} \quad (1.8)$$

$$X_{n-C8H18} = [\alpha_9 (H_{CH} - H_{CH4}) + \beta_9 (H_{CH} - H_{CH4})^2] X_{CH} \quad (1.9)$$

Here, $\alpha_i$ and $\beta_i$ are constants and $H_{CH4}$ is the molar calorific value of methane. The variable $H_{CH}$ is the molar calorific value of the sum of the specified alkanes ($H_{CH} = \Sigma X_{CH,i} H_{CH,i}$). The proportion of methane is in this case determined as follows:

$$X_{CH4} = X_{CH} - (X_{C2N6} + X_{C3H8} + X_{i-C4H10} + X_{n-C4H10} + X_{i-C5H12} + X_{n-C5H12} + X_{n-C6H14} + X_{n-C7H16} + X_{n-C8H18}) \quad (2)$$

An embodiment of the invention is characterized in that the steps a) and b) are preceded by a plurality of measurement cycles in which step (a) is carried out using a plurality of reference gases whose composition and whose selected physical property of the sum of the specified alkanes are known, in that the constants, e.g. coefficients, of the functions describing the proportion of the alkanes excluding methane are determined from the signals measured on the reference gases, in that the constants of the functions are stored with assignment to the respective alkanes and in that the proportion of the alkanes excluding methane is determined from a future measurement cycle on fuel gas of unknown composition with the aid of the functions.

In this way, the constants $\alpha_i$ and $\beta_i$ can be found with the aid of only two reference cycles for all natural gases. To increase the measurement accuracy, any number of reference cycles can be carried out. Even in the case of a large number of reference cycles, the outlay remains comparatively low since the constants $\alpha_i$ and $\beta_i$ only have to be determined once.

The proportion of the sum of the alkanes in the fuel gas can be determined with the assumption that the fuel gas consists only of a specified number of alkanes, nitrogen and carbon dioxide. The associated equations therefore have the form:

$$X_{CH}=1-X_{N2}-X_{CO2} \quad (3)$$

Here, $X_{N2}$ and $X_{CO2}$ are the proportions of nitrogen and carbon dioxide, respectively.

To increase the measurement accuracy, it can alternatively be assumed that the fuel gas additionally contains hydrogen and/or carbon monoxide. If both the proportion of hydrogen and the proportion of carbon monoxide are taken into account, equation (3) becomes:

$$X_{CH}=1-X_{N2}-X_{CO2}-X_{H2}-X_{CO} \quad (3')$$

A preferred illustrative embodiment is characterized in that the speeds of sound under three different conditions can be derived from the gas composition. These speeds of sound can be calculated in a simple way from the composition of the gas by means of an equation of state such as the AGA-8 equation frequently used for gas.

$$W_{i,calc}=f(p_i, T_i, X_{CH4}, \ldots X_{n-C8H18}, X_{CO2}, X_{N2}) \quad (4)$$

An example of an embodiment of the invention is characterized in that values for the speed of sound under three different conditions are derived from the composition of the fuel gas, in that the difference between the derived and the measured value of the speeds of sound is formed, in that, if the difference exceeds a specified threshold value, the proportion of at least one of the components of the fuel gas to be determined is altered, in that the composition is recalculated on the basis of the altered value or values, the values of the selected parameters are recalculated and the difference between these and the measured values is determined and in that the latter two steps are repeated until the difference lies below the threshold value.

It has been found that the gas composition can be determined particularly quickly in this way. If all 14 equations given above (1.1 to 4) are to be taken into account, these contain up to 14 unknowns, namely $X_{CH}$, $X_{CH4}$, $X_{C2H6}$, $X_{C3H8}, \ldots, X_{n-C8H19}, W_{1,calc}, W_{2,calc}, W_{3,calc}$. To solve these 14 equations, one or more values, e.g. the three speeds of sound mentioned, can be derived and compared with the corresponding measured value.

An advantage of the method of the invention is that not only can the calorific value be determined, but other important properties of the gas such as the real gas factor, the density, the speed of sound, the enthalpy, the methane number or the Wobbe index of the fuel gas can be calculated from the composition.

The physical parameters determined using the method of the invention are essentially as good as those determined by means of gas chromatography. According to the invention, only three measured parameters, e.g. two speeds of sound and the dielectric constant, are sufficient to carry out many process engineering calculations. Firstly, changes of state in gas reservoirs or storage volumes can be determined. In addition, the relevant gas transport data, e.g. temperature or pressure drop, can be determined. For vehicles powered by natural gas, the required design of gas filling stations can be calculated.

Fill level measurements can be checked and designed using the method of the invention.

In connection with heat exchangers too, the invention is of great advantage. The design of heat exchangers can be calculated using the method of the invention.

Performance measurements on heat exchangers can be evaluated using the method. Finally, compressor characteristics and compressor performance can be determined using the method of the invention.

In all the abovementioned applications, expensive gas-chromatographic analyses have previously been necessary.

The methane number, too, can be determined using the method of the invention. If the gas property data which were originally measured for charging purposes are used as input measurement signals for the method of the invention, the methane number can be calculated to essentially the same accuracy as when using a gas chromatograph. The deviation of the methane numbers is less than 2%.

When using the gas property data measured for changing purposes or when using supply network simulations, fuel gas customers can be informed at any time about current and possibly future fluctuations in the methane number without additional measurements. The gas transport network can also be controlled more flexibly without additional cost.

Further advantageous embodiments of the invention are characterized in the subclaims.

In the following, the use of the novel noncombustive method of measuring and/or regulating the amount of heat supplied to gas consumption devices is illustrated by means of the illustrative embodiments shown in the drawing. In the drawing.

Figure 1:
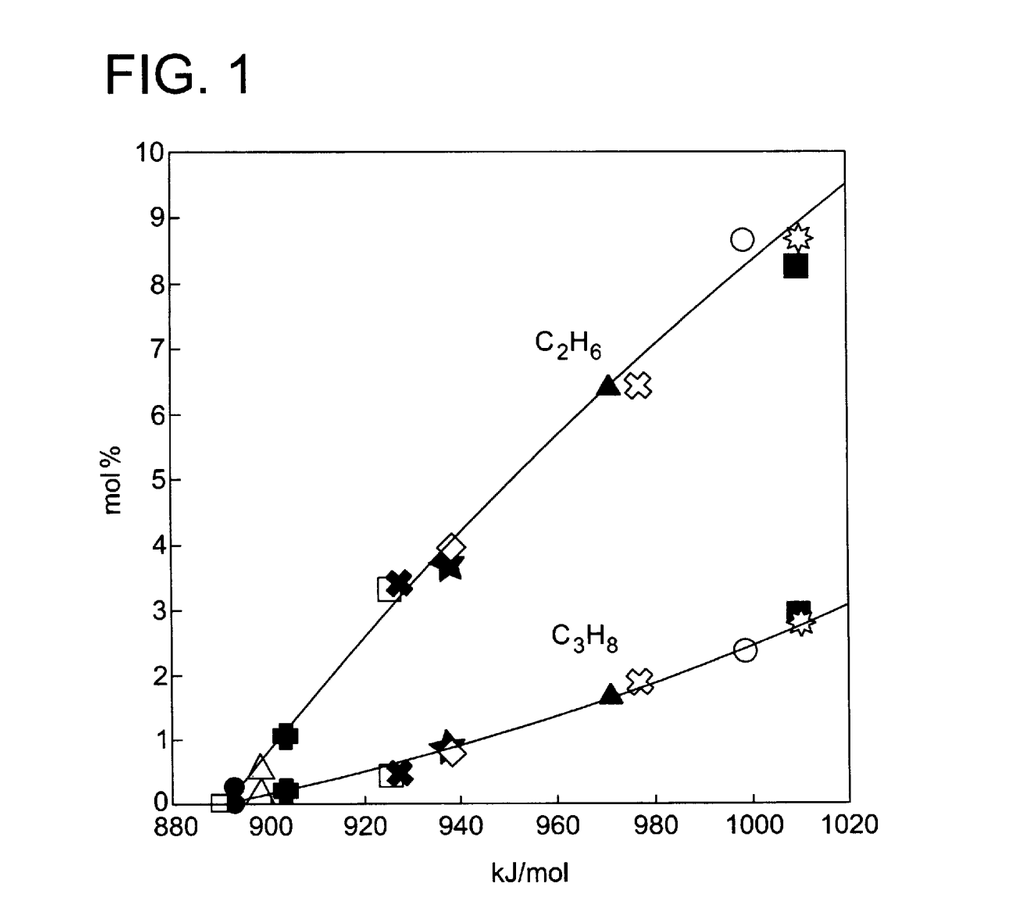
FIG. 1 shows a graph in which the mole fraction of ethane and propane for various gases is plotted against the molar calorific value of the sum of the hydrocarbons.

In FIG. 1, the molar calorific value of the sum of the alkanes ($H_{CH}$) is plotted on the x axis and the mole fraction of ethane ($C_2H_6$) and propane ($C_3H_8$) is plotted on the y axis. The corresponding values were determined for various natural gases and plotted. The proportion of both ethane and of propane was approximated by a 2nd order polynomial. As FIG. 1 shows, both the proportion of ethane and that of propane can be approximated surprisingly well by a 2nd order polynomial dependent on the molar calorific value of the sum of the alkanes. The same applies to the further alkanes up to octane. The measured values for these alkanes are, for reasons of clarity, not shown in FIG. 1.

Figure 2A:
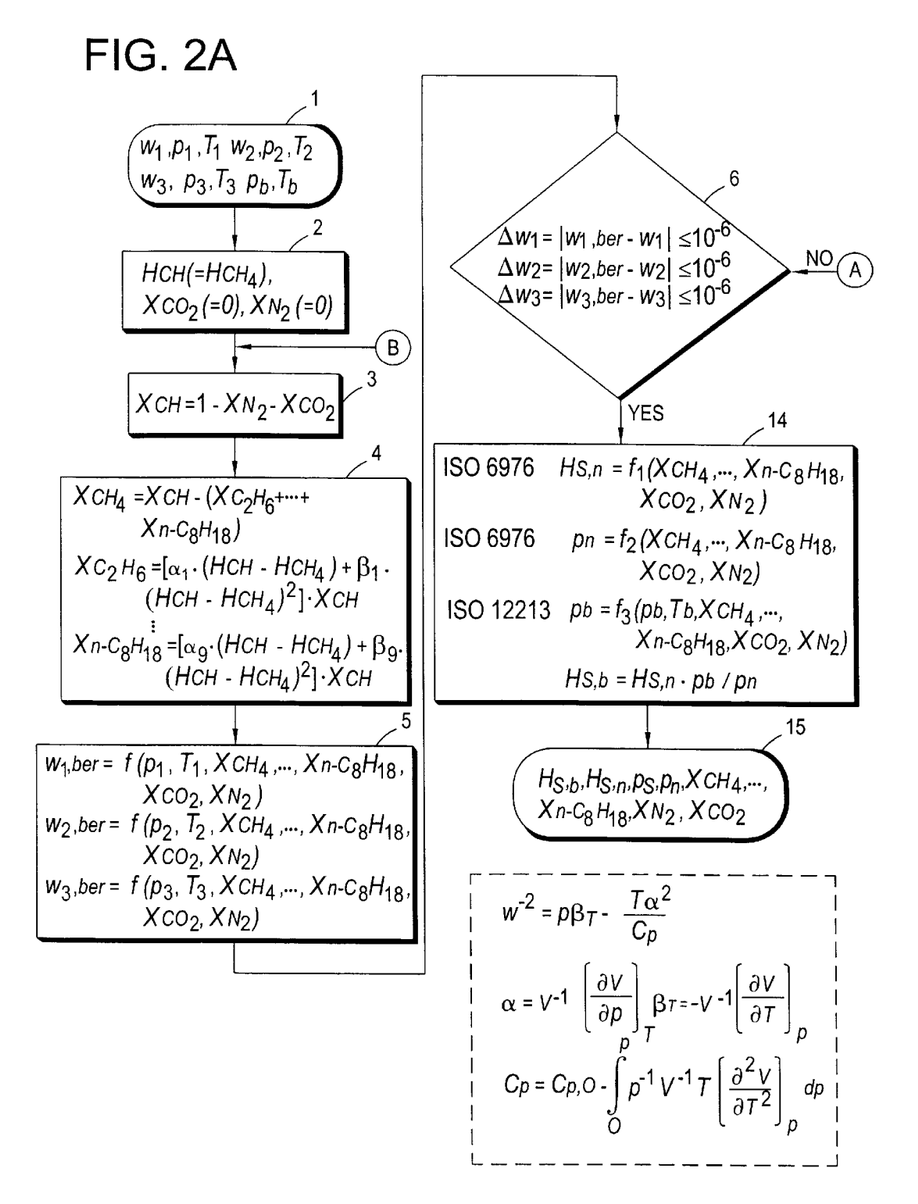
FIG. 2A and FIG. 2B show a flow diagram for the determination of the gas composition according to an illustrative embodiment of the method of the invention.
Figure 2B:
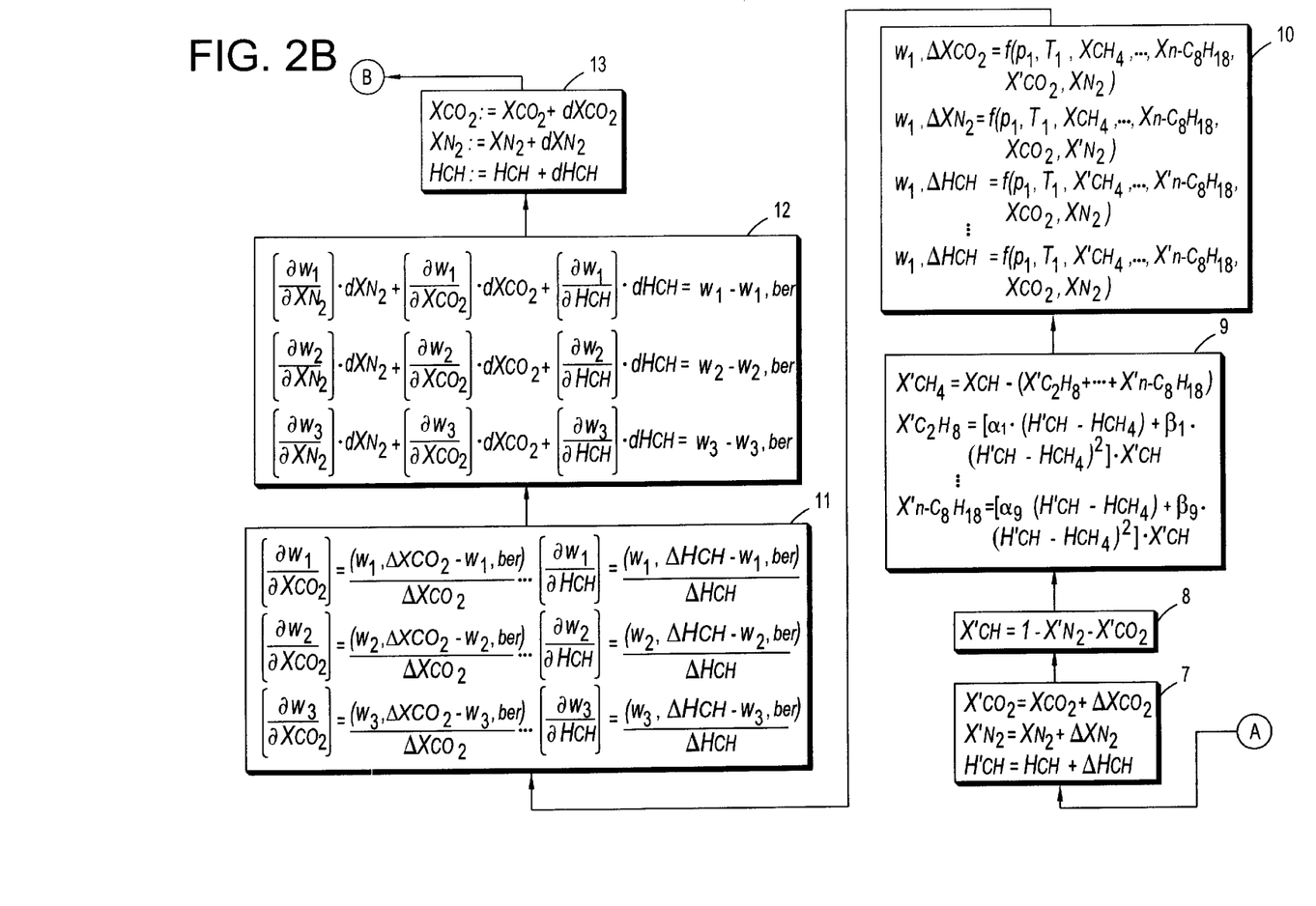

FIGS. 2A and 2B show a flow diagram for the determination of the gas composition according to a preferred illustrative embodiment.

In step 1, three speeds of sound are measured, each under different conditions. Of the conditions, the pressure is set in each case and the temperature can be set or the measurement can take place at the temperature which is established after a possible pressure change. The actual pressure and the temperature for each measurement are measured.

In step 2, starting values for the molar calorific value of the sum of the alkanes ($H_{CH}$), the proportion of nitrogen $X_{N2}$ and the proportion of carbon dioxide $X_{CO2}$ are determined. For the starting values, it is also possible to use the data for pure methane, i.e. $X_{CO2}=0$, $X_{N2}=0$ and $H_{CH}=H_{CH4}$. In practice, good results are achieved using these starting values.

Using the starting values for the proportion of nitrogen and the proportion of carbon dioxide, the proportion of the sum of the alkanes $X_{CH}$ is then determined in step 3.

In step 4, the proportion of the alkanes excluding methane is then determined with the aid of the molar calorific value of the sum of the alkanes $H_{CH}$ and the equations (1.1) to (1.9). Subsequently, the proportion of methane $X_{CH4}$ is determined using equation (2). With the aid of an equation of state, values for the speed of sound under the same conditions as for the values measured in step 1 are then calculated in step 5 from the calculated composition of the gas. This can be done, for example, with the aid of the known AGA8-DC92 equation of state.

In step 6, a check is made as to whether the absolute value of the difference between the calculated values of the speed of sound $W_{1,calc}$, $W_{2,calc}$, $W_{3,calc}$ and the values $w_1$, $w_2$, $w_3$ measured in step 1 is, for each value, less than the threshold value which has been laid down as $10^{-6}$. If not, the procedure is continued from step 6.

In steps 7 to 11, the sensitivity of the input parameters $X_{N2}$, $X_{CO2}$ and $H_{CH}$ is determined. For this purpose, values for $\Delta X_{N2}$, $\Delta X_{CO2}$ and $\Delta H_{CH}$ are first laid down in step 7. Good results are achieved using 0.1 mol % for $\Delta X_{N2}$ and $\Delta X_{CO2}$ and 1.0 MJ/mol for $\Delta H_{CH}$.

In step 8, the sum of the alkanes $X'_{CH}$ is calculated from the new values of the proportion of carbon dioxide $X'_{CO2}$ and the proportion of nitrogen $X'_{N2}$ using equation (3).

Subsequently, in step 9, the proportion of alkane excluding methane is determined using the new sum of the alkanes $X'_{CH}$ and the new molar calorific value of the sum of the alkanes $H'_{CH}$ and the equations (1.1) to (1.9) and, finally, the proportion of methane $X'_{CH4}$ is calculated by means of equation (2).

In step 10, the values of the speed of sound are determined under the three different conditions employed in step 1. Here, only one of the three input parameters is varied in each case. After completion of step 10, values for the speed of sound as a function of $X'_{CO2}$, $X'_{N2}$ and $H'_{CH}$ have thus been obtained for each condition.

Subsequently, the partial derivatives are determined in step 11. For this purpose, the change in the speed of sound as a function of one of the input parameters is first determined. For this purpose, the difference between the values of the speed of sound calculated in step 10, with one of the input parameters being changed slightly, and the value calculated in step 5 is determined. The partial derivative can now be calculated in a simple way from the quotient of the abovementioned change in the speed of sound and the change in the input parameter concerned as laid down in step 6.

In step 12, generally valid equations for describing the translation of changes in the input parameters into an output parameter are provided. After input of the values of the partial derivatives calculated in step 10 and the deviation in the output parameters calculated in step 6, the system of linear equations can be solved for the parameters $X_{N2}$, $X_{CO2}$ and $H_{CH}$ by means of generally known mathematical techniques. The result is estimates of the required changes in the parameters $X_{N2}$, $X_{CO2}$ and $H_{CH}$.

In step 13, the new values for the proportion of nitrogen $X_{N2}$, the proportion of carbon dioxide $X_{CO2}$ and the molar calorific value of the sum of the specified alkanes HCH are laid down afresh by simply adding the deviations in these three parameters calculated in step 12 to the previous values.

Steps 3 to 6 are then repeated using the freshly laid down value for the proportion of nitrogen. If, in step 6, the threshold values of $\Delta w_1$, $\Delta w_2$ an/or $\Delta w_2$ are again exceeded, steps 7 to 13 and 3 to 6 are carried out once again. Only when $\Delta w_1$, $\Delta w_2$ and $\Delta w_3$ are below the threshold value of $10^{-6}$ in step 6 are the proportions of the alkanes and the proportion of nitrogen established to the desired degree of accuracy.

In this latter case, all desired gas parameters are then calculated in steps 14 and 15. This is done with the aid of the known ISO 6976 and ISO 12213.

The method described can be carried out analogously for the combinations of two speeds of sound with the dielectric constant of the fuel gas or with the proportion of carbon dioxide in the fuel gas.

The object of the invention is also achieved by the use of the novel noncombustive method of measuring and/or regulating the amount of heat supplied to gas consumption devices, in particular to devices for consumption of natural gas, wherein, in step a), the fuel gas or a substream of the fuel gas is additionally passed through a volume or mass meter and the volume or the mass of the fuel gas supplied is measured.

For the purposes of the present invention, gas consumption devices are all necessary devices for the use of gas on the premises of private and industrial customers and also all transfer points or the like.

According to the invention, it is possible, for example, for the amount of heat supplied to domestic premises to be derived from only four parameters, viz. firstly the volume or the mass, secondly two speeds of sound and thirdly the dielectric constant or a third speed of sound or the proportion of carbon dioxide under the abovementioned conditions. The technical outlay and the costs for this are minimal.

To increase the accuracy, it is possible, as in the measurement of the calorific value, to determine as many further parameters as desired. For applications in which particularly high measurement accuracies are required, e.g. for determining the amount of heat supplied at transfer points of main transport lines having a high gas throughput, it is advantageous to measure the pressure, the temperature and the proportion of nitrogen in addition to the above three parameters. When a lower measurement accuracy is permissible, estimated values can also be used for these parameters.

Figure 3:
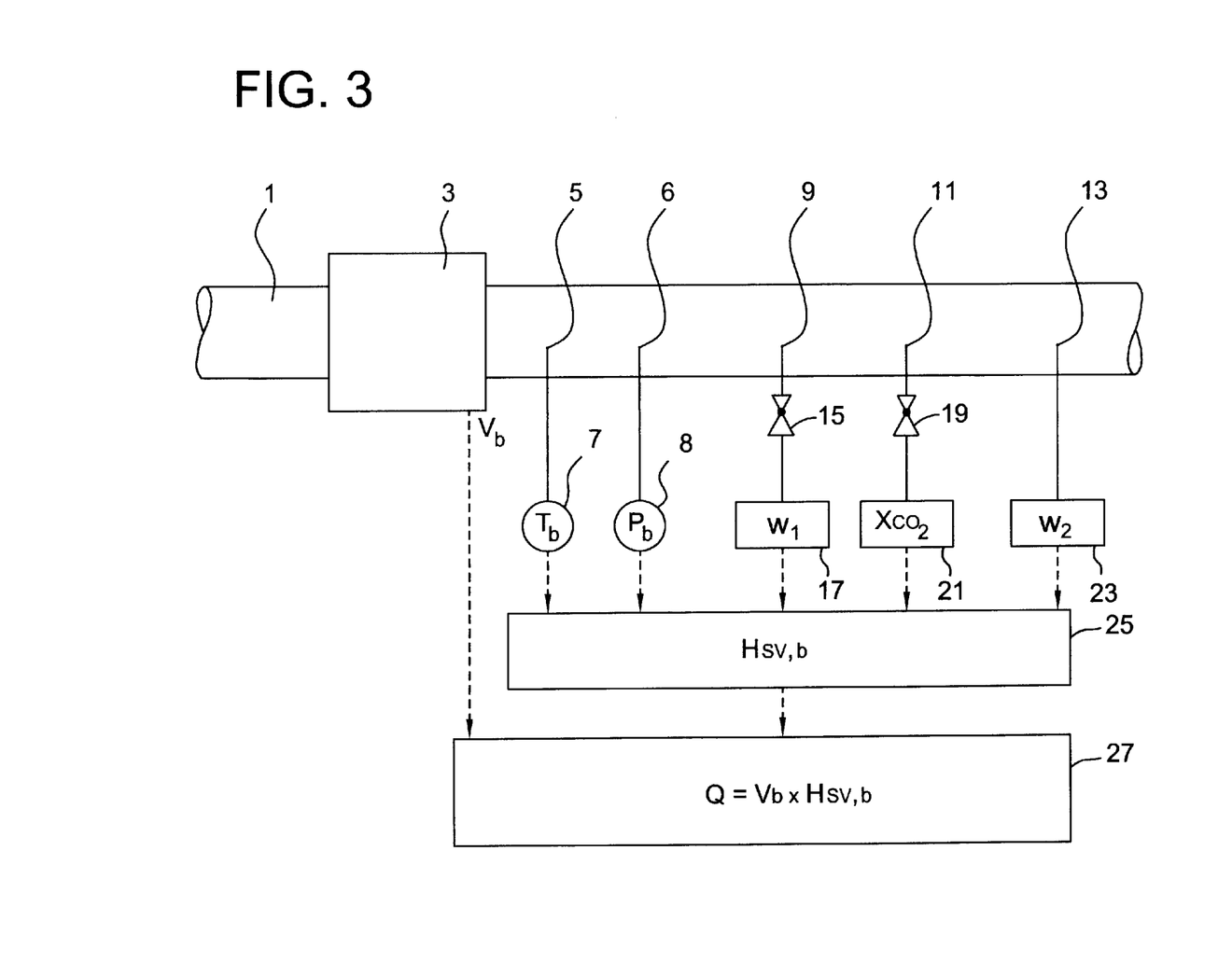
FIG. 3 shows a schematic view of an arrangement for carrying out a first illustrative embodiment of the use according to the invention of the method of measuring the calorific value.

FIG. 3 shows a fuel gas line 1 in which a gas meter 3 is located. In addition, two measurement points 5 and 6 are located in the fuel gas line 1. Measurement point 5 is provided with a temperature sensor 7 and measurement point 6 is provided with a pressure sensor 8. Furthermore, three offtake points 9, 11 and 13 are provided in the fuel gas line. Offtake point 9 is connected via a pressure-reducing valve 15 to a measuring apparatus for measuring the speed of sound under first reference conditions 17. Offtake point 11 is connected via a pressure-reducing valve 19 to a measuring apparatus for measuring the proportion of carbon dioxide 21. Offtake point 13 is connected to a measuring apparatus for measuring the speed of sound under operating conditions 23.

In the operating state, the gas meter 3 measures the volume flow and the time and, from this, calculates the volume of the fuel gas supplied. The temperature sensor 7 measures the temperature and the pressure sensor 8 measures the pressure in the fuel gas line 1.

The signal outputs of the temperature sensor 7, the pressure sensor 8 and the measuring apparatus 17, 21 and 23 are connected to the inputs of a correlation translator 25 for the correlative determination of the calorific value $H_{SV,b}$, either directly from the measured parameters or by means of the above-described iterative method.

The output of this correlation translator and the signal output of the gas meter 3 are connected to the inputs of the energy translator 27. Subsequently, the energy translator 27 calculates the amount of heat Q by multiplication of the calorific value $H_{SV,b}$ with the volume under operating conditions $V_h$. In the practical configuration, correlation translation and energy translation are integrated as successive program steps in a computer.

Figure 4:
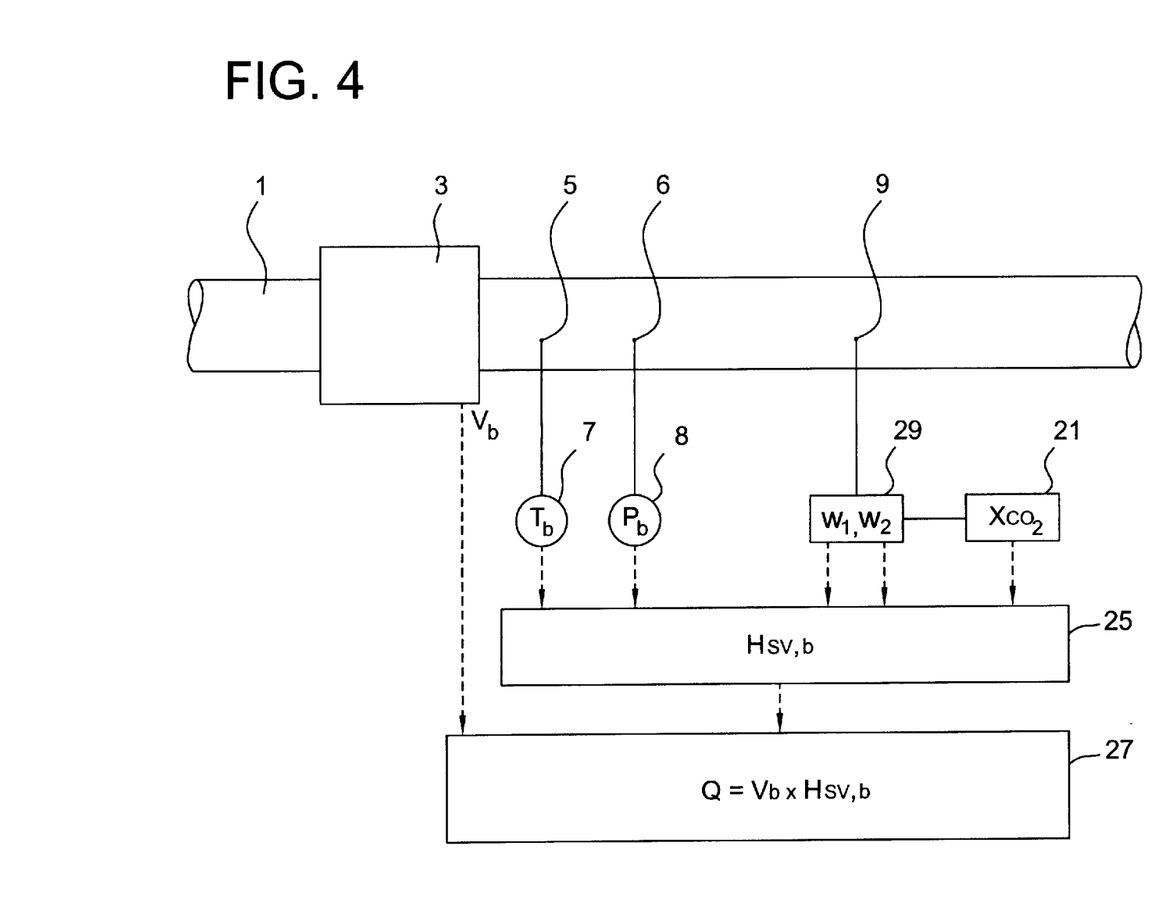
FIG. 4 shows a schematic view of an arrangement for carrying out a second illustrative embodiment of the use according to the invention.

FIG. 4 shows an arrangement for carrying out a second illustrative embodiment of the invention. The arrangement in FIG. 4 differs from the arrangement in FIG. 3 in that both speeds of sound are measured in a measuring apparatus 29 for measuring the speed of sound. The fuel gas is fed directly without a pressure reduction to the measuring apparatus 29 so that the speed of sound can be measured directly under operating conditions. Measuring apparatus 29 is provided with a means for increasing or lowering the pressure to the range of the first or second reference conditions. The measuring apparatus 29 is connected via a gas line to a measuring apparatus 21 for determining the proportion of carbon dioxide.

In this illustrative embodiment, the amount of heat is calculated by the energy translator 27 via the correlation translator 25, as in the first illustrative embodiment, on the basis of the volume, the temperature and the pressure under operating conditions, the speed of sound under first reference conditions, the speed of sound under operating conditions and the proportion of carbon dioxide. Since in both the illustrative embodiments shown in FIG. 3 and FIG. 4 the measuring apparatus for the speed of sound and the proportion of carbon dioxide are located outside the fuel gas line, maintenance of these apparatus and any repair can be carried out without any particular technical difficulty. In addition, only comparatively few reference cycles are required, since the speeds of sound are measured under specified conditions. There is thus a direct correlation between a change in the speeds of sound and a change in the gas composition.

The illustrative embodiment shown in FIG. 4 can be realised particularly inexpensively, since the speed of sound is simpler and more convenient to measure than the density of the fuel gas as is determined in most known methods.

Figure 5:
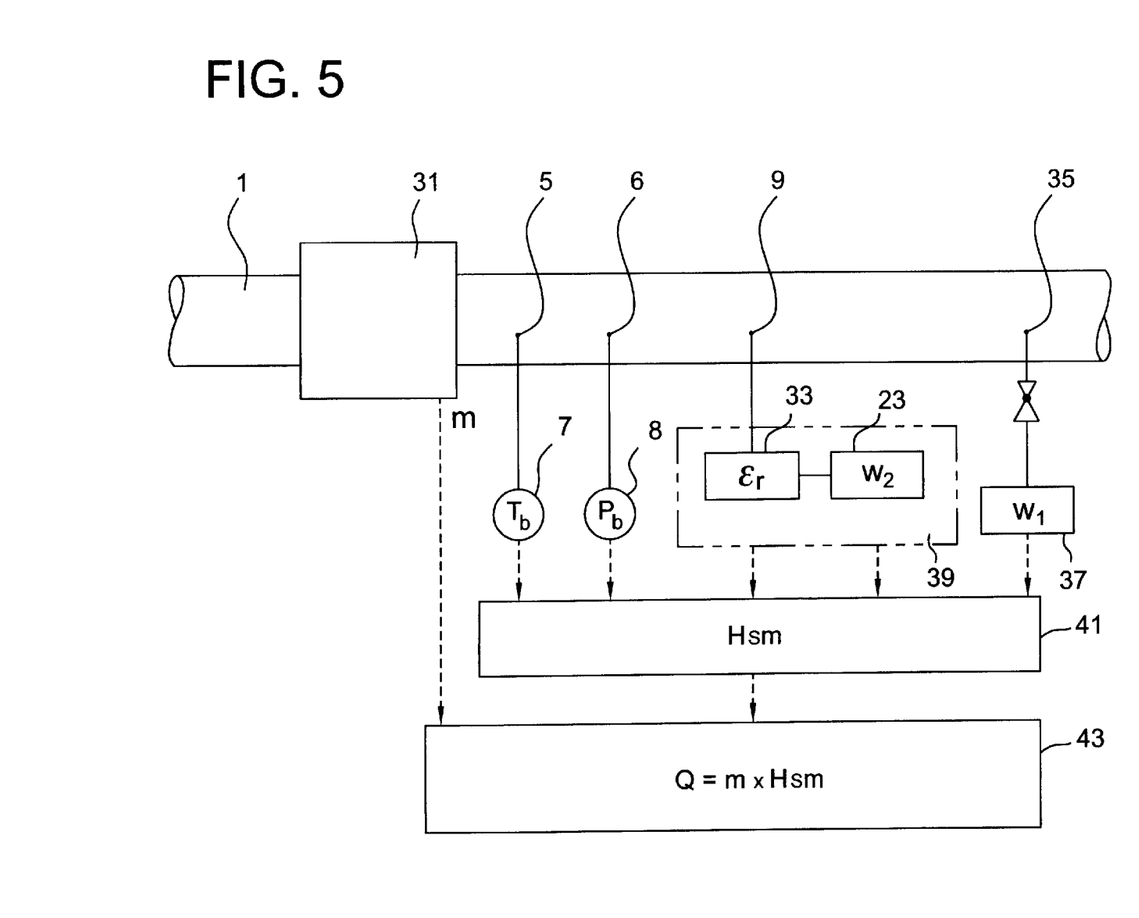
FIG. 5 shows a schematic view of an arrangement for carrying out a third illustrative embodiment of the use according to the invention.

FIG. 5 schematically shows a third illustrative embodiment of the invention. The arrangement differs from the arrangement shown in FIG. 4 in that a mass meter 31 for measuring the mass of the fuel gas supplied is provided in place of the volume meter and in that a measuring apparatus for determining the dielectric constant 33 is provided in place of a measuring apparatus for determining the proportion of carbon dioxide. In addition, the measuring apparatus for the dielectric constant measurement 33 and for measuring the speed of sound under operating conditions 23 are arranged in a joint measurement environment 39. Furthermore, a separate offtake point 35 is assigned to the measuring apparatus for determining the speed of sound under first reference conditions 37.

The correlation translator 41 first calculates the calorific value $H_{Sm}$ by correlation. Subsequently, the energy translator 43 calculates the amount of heat Q by multiplication of the calorific value $H_{Sm}$ with the mass m.

Figure 6:
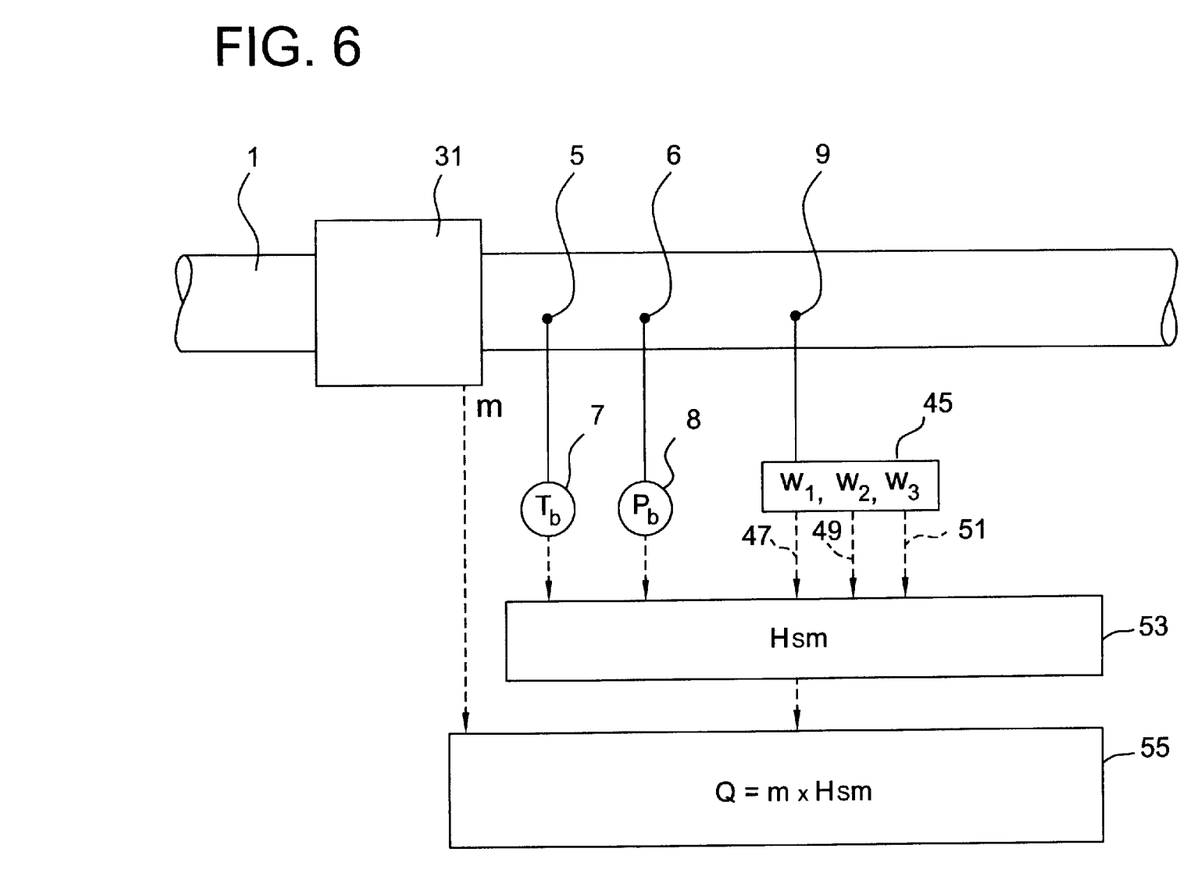
FIG. 6 shows a schematic view of an arrangement for carrying out a fourth illustrative embodiment of the use according to the invention.

In the fourth illustrative embodiment of the invention shown in FIG. 6, only one measuring apparatus 45 is provided for measuring the speed of sound. In this measuring apparatus, the speed of sound under operating conditions 47 is determined first and the speed of sound under first and third reference conditions, 49 and 51 respectively, is then measured by setting the desired pressure values. The remainder of the determination proceeds as in the previous illustrative embodiments by means of the correlation translator 53 and energy translator 55.

All illustrative embodiments have the advantage that it is not necessary to carry out measurements of the speed of sound in order to determine the amount of heat reliably, because the necessary data can be derived from the known relationships between the gas composition and the speed of sound. These known data can be utilized to derive the calorific value from the speed of sound. Furthermore, the joint measurement environment for the dielectric measurement and the measurement of the proportion of carbon dioxide and the measurements of the speed of sound has the advantage that only one pressure and temperature measurement is required in addition to the pressure and temperature measurement in the fuel gas line. The third illustrative embodiment has a particularly high accuracy in the determination of the amount of heat and is therefore particularly advantageous. It is also possible to locate some of the apparatus for determining the parameters under operating conditions inside the fuel gas line.

What is claimed is:

1. A noncombustive method for measuring the calorific value of a fuel gas which may also contain an amount of carbon dioxide and/or nitrogen gas, comprising:

a) measuring the speed of sound in the fuel gas under first and under second reference conditions and one of the parameters of dielectric constant, speed of sound under third reference conditions or the proportion of carbon dioxide in the fuel gas, and b) deriving the calorific value of said fuel gas from these three parameters, wherein the dielectric constant or the proportion of carbon dioxide and at least one value for the speed of sound are measured in a joint measuring environment.

2. The method according to claim 1, wherein the dielectric constant, the proportion of carbon dioxide, and at least one value for the speed of sound are measured in a joint measuring environment.

3. A noncombustive method for measuring the calorific value of fuel gas comprising:

a) measuring the speed of sound in the fuel gas under first and under second reference conditions and one of the parameters of dielectric constant, speed of sound under third reference conditions or the proportion of carbon dioxide in said fuel gas, and b) deriving the calorific value of said fuel gas from these three parameters, wherein the first reference conditions set for the measurement of the speed of sound are a pressure of from 1 to 10 bar and a temperature above 225 K.

4. The method according to claim 1 or 2, wherein the second reference conditions set for the measurement of the speed of sound are a pressure above 30 bar and a temperature of from 225 K to 350 K.

5. The method according to claim 1 or 3, wherein the third reference conditions set for the measurement of the speed of sound are a pressure of from 175 to 225 bar and a temperature of from 225 K to 350 K, in which case the pressure set in the measurement under the second reference conditions is below 70 bar.

6. The method according to claim 1 or 3, wherein the second reference conditions set are operating conditions.

7. The method according to claim 1 or 3, wherein in step a), at least one of the parameters of temperature, pressure or proportion of nitrogen is additionally measured.

8. The method according to claim 1 or 3, wherein said method further comprises taking off a substream of the fuel gas for the measurement of one of the speeds of sound and measuring the proportion of carbon dioxide on said substream.

9. The method according to claim 3, wherein the dielectric constant or the proportion of carbon dioxide and at least one value for the speed of sound are measured in a joint measuring environment.

10. A non-combustive method for measuring the calorific value of a fuel gas which may also contain an amount of carbon dioxide and/or nitrogen gas, comprising:

according to any of claims 1 to 8, characterized in that a) conducting a plurality of measurement cycles in which the speed of sound for each of a plurality of reference gases of known calorific value is measured under first and second sound reference conditions and one of the parameters of dielectric constant, speed of sound under third reference conditions, or the proportion of carbon dioxide in the fuel gas, wherein a number corresponding to the number of measurement cycles of reference signal patterns determined form the ratio of the various measurement signals measured on the reference gases are stored with assignment to the known calorific values;

b) measuring the speed of sound in the gas under the first and under second reference conditions and at least one of the parameters of dielectric constant, speed of sound under the third reference conditions or proportion of carbon dioxide in said fuel gas, and c) comparing the signal pattern from a measurement cycle on said fuel gas of unknown calorific value with the reference signal patterns so as to assign a particular calorific value to said fuel gas of unknown calorific value.

11. The method according to claim 10, wherein the dielectric constant or the proportion of carbon dioxide and at least one value for the speed of sound are measured in a joint measuring environment.

12. The method according to claim 9, wherein the first reference conditions set for the measurement of the speed of sound are a pressure of from 1 to 10 bar and a temperature above 225 K.

13. The method according to claim 9, wherein the second reference conditions set for the measurement of the speed of sound are a pressure above 30 bar and a temperature of from 225 K to 350 K.

14. The method according to claim 9, wherein in step b), the third reference conditions set for the measurement of the speed of sound are a pressure of from 175 to 225 bar and a temperature of from 225 K to 350 K, in which case the pressure set in the measurement under the second reference conditions is below 70 bar.

15. The method according to claim 9, wherein the second reference conditions are set to correspond with planned operating conditions.

16. The method according to claim 9, wherein at least one of the parameters temperature, pressure or proportion of nitrogen is additionally measured.

17. The method according to claim 9, wherein said method further comprises taking off a substream of the fuel gas of unknown calorific value for measuring one of the speeds of sound, and measuring the proportion of carbon dioxide on said substream.

18. The method according to claim 1 or 3 for the non-combustive measurement and/or regulation of the amount of heat supplied to a gas consumption device, in particular to devices for consumption of natural gas, wherein, in step a), the fuel gas or a substream of the fuel gas is additionally passed through a volume or mass meter and the volume or the mass of the fuel gas supplied is measured.

19. The method according to claim 9 for the noncombustive measurement and/or regulation of the amount of heat supplied to a gas consumption device, in particular to devices for consumption of natural gas, wherein, in step b), the fuel gas or a substream of the fuel gas is additionally passed through a volume or mass meter and the volume or the mass of the fuel gas supplied is measured.

* * * * *